United States Patent
Roy et al.

(10) Patent No.: US 11,246,824 B2
(45) Date of Patent: Feb. 15, 2022

(54) COSMETIC COMPOSITION COMPRISING A PARTICULAR COMBINATION OF SURFACTANTS, A SILICONE, A CATIONIC POLYMER, A FATTY ALCOHOL AND A CLAY

(71) Applicant: L'Oreal, Paris (FR)

(72) Inventors: Dhimoy Roy, Kanagawa (JP); Maxime De Boni, Shanghai (CN); Lakshay Mohindroo, Chembur (IN)

(73) Assignee: L'Oreal, Paris (FR)

( * ) Notice: Subject to any disclaimer, the term of this patent is extended or adjusted under 35 U.S.C. 154(b) by 223 days.

(21) Appl. No.: 16/314,836

(22) PCT Filed: Jul. 4, 2017

(86) PCT No.: PCT/EP2017/066570
§ 371 (c)(1),
(2) Date: Jan. 2, 2019

(87) PCT Pub. No.: WO2018/007352
PCT Pub. Date: Jan. 11, 2018

(65) Prior Publication Data
US 2019/0307669 A1      Oct. 10, 2019

(30) Foreign Application Priority Data
Jul. 7, 2016   (IN) .............................. 201611023276

(51) Int. Cl.
| | | |
|---|---|---|
| *A61K 8/00* | (2006.01) | |
| *A61K 8/898* | (2006.01) | |
| *A61K 8/26* | (2006.01) | |
| *A61K 8/34* | (2006.01) | |
| *A61K 8/41* | (2006.01) | |
| *A61K 8/44* | (2006.01) | |
| *A61K 8/73* | (2006.01) | |
| *A61K 8/86* | (2006.01) | |
| *A61K 8/891* | (2006.01) | |
| *A61Q 5/02* | (2006.01) | |
| *A61Q 19/10* | (2006.01) | |

(52) U.S. Cl.
CPC ............... *A61K 8/898* (2013.01); *A61K 8/26* (2013.01); *A61K 8/342* (2013.01); *A61K 8/416* (2013.01); *A61K 8/442* (2013.01); *A61K 8/737* (2013.01); *A61K 8/86* (2013.01); *A61K 8/891* (2013.01); *A61Q 5/02* (2013.01); *A61Q 19/10* (2013.01); *A61K 2800/5426* (2013.01)

(58) Field of Classification Search
CPC .......... A61K 8/898; A61K 8/26; A61K 8/342; A61K 8/416; A61K 8/737; A61Q 5/02
See application file for complete search history.

(56) References Cited

U.S. PATENT DOCUMENTS

| | | | |
|---|---|---|---|
| 5,846,549 A | 12/1998 | Beauquey et al. | |
| 8,038,989 B2 * | 10/2011 | Murray .................... | A61K 8/86 424/70.27 |
| 2009/0048132 A1* | 2/2009 | Paul ....................... | A61K 8/442 510/127 |
| 2009/0074700 A1* | 3/2009 | Nguyen ................... | A61Q 5/00 424/70.17 |
| 2009/0233825 A1* | 9/2009 | Giles ....................... | A61K 8/042 510/123 |
| 2012/0021025 A1* | 1/2012 | Bendejacq ............. | A61K 8/891 424/401 |

FOREIGN PATENT DOCUMENTS

| | | |
|---|---|---|
| DE | 10 2013 226 269 A1 | 7/2015 |
| DE | 10 2014 224 770 A1 | 10/2015 |
| EP | 0 858 794 A2 | 8/1998 |
| EP | 2 153 818 A2 | 2/2010 |
| JP | 2004-262805 A | 9/2004 |
| JP | 2006-104149 A | 4/2006 |

OTHER PUBLICATIONS

Database GNPD [Online} Mintel: Jul. 31, 2012, Anonymous: "Thickening shampoo," XP002772780, Database Accession No. 1824403, 4 pages.
International Search Report dated Aug. 18, 2017, issued in corresponding International Application No. PCT/EP2017/066570, filed Jul. 4, 2017, 3 pages.

* cited by examiner

*Primary Examiner* — Necholus Ogden, Jr.
(74) *Attorney, Agent, or Firm* — Christensen O'Connor Johnson Kindness PLLC

(57) ABSTRACT

The present invention relates to a composition comprising one or more cationic surfactants, one or more amphoteric or zwitterionic surfactants, one or more silicones, one or more cationic polymers, one or more fatty alcohols and one or more clays. The invention also relates to a cosmetic process for washing keratin fibres using this composition. Finally, the invention relates to the use of such a composition for washing keratin fibres.

17 Claims, No Drawings

COSMETIC COMPOSITION COMPRISING A PARTICULAR COMBINATION OF SURFACTANTS, A SILICONE, A CATIONIC POLYMER, A FATTY ALCOHOL AND A CLAY

The present invention relates to a cosmetic composition useful for washing keratin fibres, and in particular human keratin fibres such as the hair, which comprises one or more cationic and one or more amphoteric or zwitterionic surfactants, one or more silicones, one or more cationic polymers, one or more fatty alcohols and at least one clay, preferably kaolinite, even better kaolin.

The invention also relates to a cosmetic process for washing keratin fibres using such a composition.

Finally, the invention relates to the use of such a composition for washing keratin fibres.

It is common practice to use detergent cosmetic compositions such as shampoos and shower gels, based essentially on surfactants, for washing keratin materials such as the hair and the skin. These compositions are applied to the keratin materials, which are preferably wet, and the lather generated by massaging or rubbing with the hands or a toiletry flannel makes it possible, after rinsing with water, to remove the diverse types of soiling initially present on the hair or the skin.

These compositions contain substantial contents of "detergent" surfactants, which, in order to be able to formulate cosmetic compositions with good washing power, must especially give them good foaming power.

The surfactants that are useful for this purpose are generally of anionic, non ionic and/or amphoteric type, and particularly of anionic type.

Admittedly these compositions have a good washing power, but the intrinsic cosmetic properties associated with them nevertheless remain fairly poor, owing in particular to the fact that the relatively aggressive nature of such a cleaning treatment can, in the long run, lead to more or less pronounced damage to the keratin fibres, this damage being associated in particular with the gradual removal of the lipids or proteins contained in or on the surface of said fibres.

Such damage to the hair leads to increased hair breakage in particular during combing.

Thus, there is a real need to provide compositions for washing keratin fibres, and in particular human keratin fibres, that do not have the drawbacks described above, and in particular which are milder than those of the prior art, and lead to a reduction of hair breakage, in particular a reduction the breakage that occurs during combing after the shampoo.

There is also a need to provide compositions containing reduced amounts of anionic surfactants.

The composition should also have good detergent properties, and present a good tolerance especially with respect to the skin, mucous membranes, the scalp and the eyes.

Such compositions should furthermore have good properties of use such as good foaming properties, and enhance the cosmetic properties of the keratin fibres, namely by affording them softness, smoothness and disentangling.

The Applicant has now discovered that a cosmetic composition comprising one or more cationic and one or more amphoteric or zwitterionic surfactants, one or more silicones, one or more cationic polymers, one or more fatty alcohols and a clay, makes it possible to achieve the objectives outlined above.

Thus, the subject of the invention is especially a cosmetic composition comprising:
one or more cationic surfactants,
one or more amphoteric or zwitterionic surfactants,
one or more silicones,
one or more cationic polymers,
one or more fatty alcohols, and
one or more clays.

The composition according to the invention has very good cleaning properties. It especially provides a homogeneous foam which has a good persistence over time.

Furthermore, the foam formed from the composition according to the invention spreads easily and uniformly onto keratin fibres.

In addition, the composition salts according to the invention leads to improved cosmetic properties, and especially affords good conditioning of keratin fibres such as the hair, including when these fibres are sensitized. Indeed, the composition of the invention provides, for instance, smoothness, softness and disentangling to the hair. The fibres are easy to disentangle without substantial breaking thereof.

The invention also relates to a cosmetic process for washing keratin fibres using this composition.

Finally, the invention relates to the use of such a composition for washing keratin fibres.

Other subjects, characteristics, aspects and advantages of the invention will emerge even more clearly on reading the description and the example that follows.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more".

Cationic Surfactants

The cosmetic composition comprises one or more cationic surfactants.

The term "cationic surfactant" means a surfactant that is positively charged when it is contained in the composition according to the invention. This surfactant may bear one or more positive permanent charges or may contain one or more cationizable functions in the composition according to the invention.

The cationic surfactants are preferably chosen from primary, secondary or tertiary fatty amines, optionally polyoxyalkylenated, or salts thereof, and quaternary ammonium salts, and mixtures thereof.

The fatty amines generally comprise at least one $C_8$-$C_{30}$ hydrocarbon-based chain, and preferably a $C_{12}$-$C_{22}$ alkyl chain.

As example of fatty amines, mention may be made of stearamidopropyl dimethylamine.

Examples of quaternary ammonium salts that may especially be mentioned include:

quaternary ammonium salts of general formula (IV)

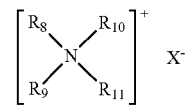

(IV)

wherein, $R_8$ to $R_{11}$, which may be identical or different, represent a linear or branched aliphatic group comprising from 1 to 30 carbon atoms, or an aromatic group such as aryl or alkylaryl, it being understood that at least one of the groups $R_8$ to $R_{11}$ comprises from 12 to 22 carbon atoms, and preferably from 16 to 22 carbon atoms; and $X^-$ represents an organic or mineral anionic counterion, such as that chosen from halides, acetates, phosphates, nitrates, $(C_1-C_4)$alkyl sulfates, $(C_1-C_4)$alkyl- or $(C_1-C_4)$alkylaryl sulfonates.

The aliphatic groups may comprise heteroatoms especially such as oxygen, nitrogen, sulfur and halogens. The aliphatic groups are chosen, for example, from $C_1-C_{30}$ alkyl, $C_1-C_{30}$ alkoxy, polyoxy$(C_2-C_6)$alkylene, $C_1-C_{30}$ alkylamide, $(C_{12}-C_{22})$alkylamido$(C_2-C_6)$alkyl, $(C_{12}-C_{22})$alkyl acetate and $C_1-C_{30}$ hydroxyalkyl groups; $X^-$ is an anion chosen from the group of halides, phosphates, acetates, lactates, $(C_1-C_4)$alkyl sulfates, and $(C_1-C_4)$alkyl- or $(C_1-C_4)$ alkylarylsulfonates.

Among the quaternary ammonium salts of formula (IV), those that are preferred are, on the one hand, tetraalkylammonium salts, for instance dialkyldimethylammonium or alkyltrimethylammonium salts in which the alkyl group contains approximately from 16 to 22 carbon atoms, in particular behenyltrimethylammonium, distearyldimethylammonium, cetyltrimethylammonium or benzyldimethylstearylammonium salts, or, on the other hand, the palmitylamidopropyltrimethylammonium salt, the stearamidopropyltrimethylammonium salt, the stearamidopropyldimethylcetearylammonium salt, or the stearamidopropyldimethyl(myristyl acetate)ammonium salt sold under the name Ceraphyl® 70 by the company Van Dyk. It is particularly preferred to use the chloride salts of these compounds.

quaternary ammonium salts of imidazoline, for instance, those of formula (V)

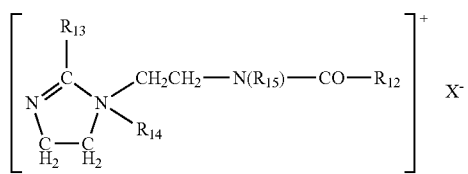

wherein, $R_{12}$ represents an alkyl or alkenyl group comprising from 8 to 30 carbon atoms, derived for example from tallow fatty acids, $R_{13}$ represents a hydrogen atom, a $C_1-C_4$ alkyl group or an alkyl or alkenyl group comprising from 8 to 30 carbon atoms, $R_{14}$ represents a $C_1-C_4$ alkyl group, $R_{15}$ represents a hydrogen atom or a $C_1-C_4$ alkyl group; $X^-$ is an anion chosen from the group of halides, phosphates, acetates, lactates, alkyl sulfates, alkyl- or alkylarylsulfonates in which the alkyl and aryl groups each preferably comprise from 1 to 20 carbon atoms and from 6 to 30 carbon atoms.

$R_{12}$ and $R_{13}$ preferably denote a mixture of alkyl or alkenyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name Rewoquat® W 75 by the company Rewo;

di- or tri-quaternary ammonium salts, in particular of formula (VI)

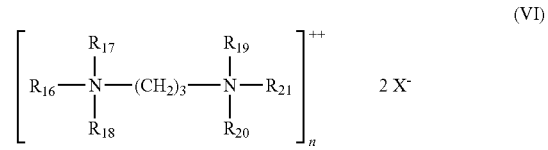

wherein, $R_{16}$ denotes an alkyl radical comprising approximately from 16 to 30 carbon atoms which is optionally hydroxylated and/or interrupted by one or more oxygen atoms, $R_{17}$ is chosen from hydrogen and an alkyl radical comprising from 1 to 4 carbon atoms and an $(R_{16a})(R_{17a})(R_{18a})N$—$(CH_2)_3$ group, $R_{16a}$, $R_{17a}$, $R_{18a}$, $R_{18}$, $R_{19}$, $R_{20}$ and $R_{21}$, which may be identical or different, are chosen from hydrogen and an alkyl radical comprising from 1 to 4 carbon atoms and $X^-$ is an anion chosen from the group of halides, acetates, phosphates, nitrates and methyl sulfates.

Such compounds are, for example, Finquat CT-P, available from the company Finetex (Quaternium 89), and Finquat CT, available from the company Finetex (Quaternium 75), quaternary ammonium salts containing at least one ester function, such as those of formula (VII)

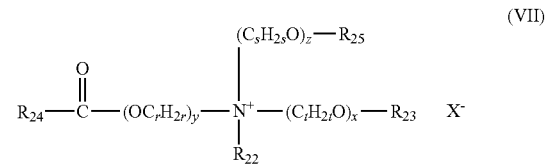

wherein, $R_{22}$ is chosen from $C_1-C_6$ alkyl groups and $C_1-C_6$ hydroxyalkyl or dihydroxyalkyl groups;

$R_{23}$ is chosen from:
the group

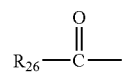

groups $R_{27}$, which are linear or branched, saturated or unsaturated $C_1-C_{22}$ hydrocarbon-based groups,
a hydrogen atom, $R_{25}$ is chosen from:
the group

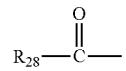

groups $R_{29}$, which are linear or branched, saturated or unsaturated $C_1-C_6$ hydrocarbon-based groups,
a hydrogen atom, $R_{24}$, $R_{26}$ and $R_{28}$, which may be identical or different, are chosen from linear or branched, saturated or unsaturated $C_7-C_{21}$ hydrocarbon-based groups;

r, s and t, which may be identical or different, are integers ranging from 2 to 6;
y is an integer ranging from 1 to 10;
x and z, which may be identical or different, are integers ranging from 0 to 10;
$X^-$ is a simple or complex, organic or mineral anion;
with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is an $R_{27}$ hydrocarbon-based group, it may be long and may contain from 12 to 22 carbon atoms, or may be short and may have from 1 to 3 carbon atoms.

When $R_{25}$ is an $R_{29}$ hydrocarbon-based group, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion compatible with the ammonium containing an ester function.

The anion $X^-$ is even more particularly chloride or methyl sulfate.

Use is made more particularly in the composition according to the invention of the ammonium salts of formula (VII) wherein:
$R_{22}$ denotes a methyl or ethyl group;
x and y are equal to 1;
z is equal to 0 or 1;
r, s and t are equal to 2;
$R_{23}$ is chosen from:
  the group

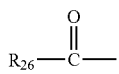

methyl, ethyl or $C_{14}$-$C_{22}$ hydrocarbon-based groups;
  a hydrogen atom;
$R_{25}$ is chosen from:
  the group

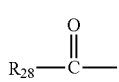

a hydrogen atom;
$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

The hydrocarbon-based groups are advantageously linear.

Mention may be made, for example, of the compounds of formula (VII) such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are obtained more particularly from a plant oil, such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with $C_{10}$-$C_{30}$ fatty acids or with mixtures of $C_{10}$-$C_{30}$ fatty acids of plant or animal origin, or by transesterification of the methyl esters thereof. This esterification is followed by quaternization using an alkylating agent such as an alkyl (preferably methyl or ethyl) halide, a dialkyl (preferably methyl or ethyl) sulfate, methyl methanesulfonate, methyl para-toluenesulfonate, glycol chlorohydrin or glycerol chlorohydrin.

Such compounds are, for example, sold under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in U.S. Pat. Nos. 4,874,554 and 4,137,180.

Use may be made of behenoylhydroxypropyltrimethylammonium chloride, provided by Kao under the name Quatarmin BTC 131.

Preferably, the ammonium salts containing at least one ester function contain two ester functions.

Among the quaternary ammonium salts containing at least one ester function, which may be used, it is preferred to use dipalmitoylethylhydroxyethylmethylammonium salts.

Preferably, the cationic surfactants are chosen from quaternary ammonium salts of general formula (IV) and mixtures thereof.

Better still, the cationic surfactants are chosen from behentrimonium chloride, cetrimonium chloride and mixtures thereof.

The amount of cationic surfactants in the composition of the present invention, advantageously ranges from 0.05 to 10% by weight, more preferentially from 0.01 to 5% by weight, and even more preferably from 0.1 to 2% by weight, relative to the total weight of the composition.

Amphoteric or Zwitterionic Surfactants

The composition according to the present invention further comprises one or more amphoteric or zwitterionic surfactant(s).

The amphoteric or zwitterionic surfactant(s) that may be used in the present invention may especially be secondary or tertiary aliphatic amine derivatives, optionally quaternized, in which the aliphatic group is a linear or branched chain containing from 8 to 22 carbon atoms, the said amine derivatives containing at least one anionic group, for instance a carboxylate, sulfonate, sulphate, phosphate or phosphonate group. Mention may be made in particular of ($C_8$-$C_{20}$)alkylbetaines, sulfobetaines, ($C_8$-$C_{20}$alkyl)amido ($C_3$-$C_8$alkyl)betaines or ($C_8$-$C_{20}$alkyl)amido($C_6$-$C_{20}$alkyl) sulfobetaines.

Among the secondary or tertiary aliphatic amine derivatives, optionally quaternized, that may be used, as defined above, mention may also be made of the compounds of respective structures (II) and (III) below:

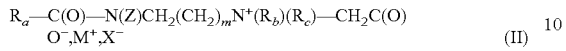
(II)

wherein,
$R_a$ represents a $C_6$-$C_{30}$ alkyl or alkenyl group derived from an acid $R_a$COOH preferably present in hydrolysed coconut oil, or a heptyl, nonyl or undecyl group;
$R_b$ represents a beta-hydroxyethyl group;
$R_c$ represents a carboxymethyl group;
$M^+$ represents a cationic counterion derived from an alkali metal or alkaline-earth metal, such as sodium, an ammonium ion or an ion derived from an organic amine; and
$X^-$ represents an organic or mineral anionic counterion, preferably chosen from halides, acetates, phosphates, nitrates, ($C_1$-$C_4$)alkyl sulphates, ($C_1$-$C_4$)alkyl or ($C_1$-$C_4$)alkylaryl sulfonates, in particular methyl sulphate and ethyl sulphate;
m is equal to 0, 1 or 2; and
Z represents a hydrogen atom or a hydroxyethyl or carboxymethyl group.
Or alternatively $M^+$ and $X^-$ are absent;

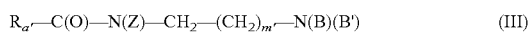
(III)

wherein
B represents the group —$CH_2$—$CH_2$—O—X';
B' represents the group —($CH_2$)$_z$Y', with z=1 or 2;
X' represents the group —$CH_2$—C(O)OH, —$CH_2$—C(O)OZ', —$CH_2$—$CH_2$—C(O)OH, —$CH_2$—$CH_2$—C(O)OZ', or a hydrogen atom;
Y' represents the group —C(O)OH, —C(O)OZ', —$CH_2$—CH(OH)—$SO_3$H or the group —$CH_2$—CH(OH)—$SO_3$—Z';
Z' represents a cationic counterion derived from an alkali metal or alkaline-earth metal, such as sodium, an ammonium ion or an ion derived from an organic amine;
$R_{a'}$ represents a $C_6$-$C_{30}$ alkyl or $C_6$-$C_{30}$ alkenyl group of an acid $R_{a'}$—COOH, which is preferably present in coconut oil or in hydrolysed linseed oil, or an alkyl group, especially a $C_{17}$ alkyl group and its iso form, or an unsaturated $C_{17}$ group;
m' is equal to 0, 1 or 2; and
Z represents a hydrogen atom or a hydroxyethyl or carboxymethyl group.

The compounds of this type are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, cocoamphodipropionic acid and hydroxyethylcarboxymethylcocamidopropylamine.

Examples that may be mentioned include the cocoamphodiacetate sold by the company Rhodia under the trade name Miranol® C2M Concentrate or under the trade name Miranol Ultra C 32 and the product sold by the company Chimex under the trade name Chimexane HA.

Use may also be made of compounds of formula (III'):

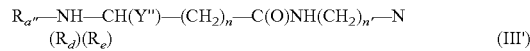
(III')

wherein,
Y" represents the group —C(O)OH, —C(O)OZ", —$CH_2$—CH(OH)—$SO_3$H or the group $CH_2$—CH(OH)—$SO_3$—Z";
$R_d$ and $R_e$, independently of each other, represent a $C_1$-$C_4$ alkyl or hydroxyalkyl radical;
Z" represents a cationic counterion derived from an alkali metal or alkaline-earth metal, such as sodium, an ammonium ion or an ion derived from an organic amine;
$R_{a''}$ represents a $C_6$-$C_{30}$ alkyl or alkenyl group of an acid $R_{a''}$—C(O)OH which is preferably present in coconut oil or in hydrolysed linseed oil; and
n and n' denote, independently of each other, an integer ranging from 1 to 3.

Among the compounds of formula (III'), mention may be made of the compound classified in the CTFA dictionary under the name sodium diethylaminopropyl cocoaspartamide and sold by the company Chimex under the name Chimexane HB.

Among the abovementioned amphoteric or zwitterionic surfactants, it is preferred to use ($C_8$-$C_{20}$ alkyl)betaines such as cocoylbetaine, ($C_8$-$C_{20}$ alkyl)amido($C_2$-$C_8$ alkyl)betaines such as cocoylamidopropylbetaine, and mixtures thereof.

More preferentially, the amphoteric or zwitterionic surfactant(s) are chosen from ($C_8$-$C_{20}$ alkyl)amido($C_2$-$C_8$ alkyl) betaines, and even more cocoylamidopropylbetaine.

The amount of the amphoteric or zwitterionic surfactant(s) advantageously ranges from 0.05% to 15% by weight, more preferentially from 0.1% to 10% by weight, and even more preferably from 0.5 to 5% by weight, relative to the total weight of the composition.

Silicones

The composition according to the present invention further comprises one or more silicones. Such silicones can be chosen in particular from non-amino silicones, amino silicones and mixtures thereof.

In the present invention, the term "silicone" is intended to denote, in accordance with what is generally accepted, any organosilicon polymer or oligomer of linear or cyclic, branched or crosslinked structure, of variable molecular weight, obtained by polymerization and/or polycondensation of suitably functionalized silanes, and consisting essentially of a repetition of main units in which the silicon atoms are linked together via oxygen atoms (siloxane bond —Si—O—Si—), optionally substituted hydrocarbon-based radicals being directly linked via a carbon atom to the said silicon atoms. The hydrocarbon-based radicals that are the most common are alkyl radicals, especially $C_1$-$C_{10}$ alkyl radicals, and in particular methyl, fluoroalkyl radicals, the alkyl part of which is $C_1$-$C_{10}$, and aryl radicals and in particular phenyl.

According to the present invention, the term "non-amino silicone" denotes any silicone not containing at least one primary, secondary or tertiary amine, or a quaternary ammonium group.

The non-amino silicones, which can be used in the composition according to the invention, are, in particular, polyorganosiloxanes that may be in the form of oils, waxes, resins or gums.

Organopolysiloxanes are defined in greater detail in Walter Noll's *Chemistry and Technology of Silicones* (1968), Academic Press.

The silicones may be volatile or non-volatile.

When they are volatile, the silicones are more particularly chosen from those with a boiling point of between 60° C. and 260° C., and even more particularly from:

(i) cyclic silicones comprising from 3 to 7 and preferably 4 to 5 silicon atoms.

These are, for example, octamethylcyclotetrasiloxane sold especially under the name Volatile Silicone 7207 by the company Union Carbide or Silbione 70045 V 2 by the company Rhodia, decamethylcyclopentasiloxane sold under the name Volatile Silicone 7158 by the company Union Carbide, and Silbione 70045 V 5 by the company Rhodia, and mixtures thereof.

Mention may also be made of cyclocopolymers of the dimethylsiloxane/methylalkylsiloxane type, such as Volatile Silicone FZ 3109 sold by the company Union Carbide, of chemical structure:

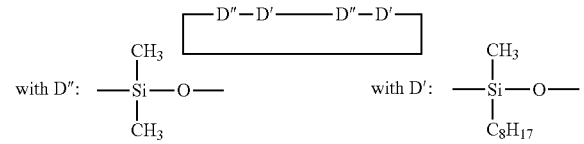

Mention may also be made of mixtures of cyclic silicones with organosilicon compounds, such as the mixture of octamethyl-cyclotetrasiloxane and tetrakis(trimethylsilyl)-pentaerythritol (50/50) and the mixture of octamethylcyclotetrasiloxane and oxy-1,1'-bis(2,2,2',2',3,3'-hexatrimethyl-silyloxy)neopentane;

(ii) linear volatile silicones containing 2 to 9 silicon atoms and having a viscosity of less than or equal to $5\times10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers *Volatile Silicone Fluids for Cosmetics*.

When the silicones are non-volatile, use is preferably made of polyalkylsiloxanes, polyarylsiloxanes, polyalkylarylsiloxanes, silicone gums and resins, and polyorganosiloxanes modified with organofunctional groups, and mixtures thereof.

These silicones are more particularly chosen from polyalkylsiloxanes, among which mention may be made mainly of polydimethylsiloxanes containing trimethylsilyl end groups (Dimethicone according to the CTFA name) having a viscosity of from $5\times10^{-6}$ to 2.5 m$^2$/s at 25° C. and preferably $1\times10^{-5}$ to 1 m$^2$/s. The viscosity of the silicones is measured, for example, at 25° C. according to standard ASTM 445 Appendix C.

Among these polyalkylsiloxanes, mention may be made, in a non-limiting manner, of the following commercial products:
- the Silbione oils of the 47 and 70 047 series or the Mirasil oils sold by the company Rhodia, for instance the oil 70 047 V 500 000,
- the oils of the Mirasil series sold by the company Rhodia,
- the oils of the 200 series from the company Dow Corning, such as, more particularly, DC200 with a viscosity of 60 000 cSt,
- the Viscasil oils from the company General Electric and certain oils of the SF series (SF 96, SF 18) from the company General Electric.

Mention may also be made of polydimethylsiloxanes containing dimethylsilanol end groups (Dimethiconol according to the CTFA name) such as the oils of the 48 series from the company Rhodia.

Mention may also be made of polydimethylsiloxanes containing α,ω-silanol groups.

In this category of polyalkylsiloxanes, mention may also be made of the products sold under the names Abil Wax 9800 and 9801 by the company Goldschmidt, which are poly(C$_1$-C$_{20}$)alkylsiloxanes.

The polyalkylarylsiloxanes are particularly chosen from linear and/or branched polydimethylmethylphenylsiloxanes and polydimethyldiphenylsiloxanes with a viscosity of from $1\times10^{-5}$ to $5\times10^{-2}$ m$^2$/s at 25° C.

Among these polyalkylarylsiloxanes, examples that may be mentioned include the products sold under the following names:
- Silbione oils of the 70 641 series from the company Rhodia,
- the oils of the Rhodorsil 70 633 and 763 series from the company Rhodia,
- the oil Dow Corning 556 Cosmetic Grade Fluid from the company Dow Corning,
- silicones of the PK series from the company Bayer, such as the product PK20,
- the silicones of the PN and PH series from the company Bayer, such as the products PN1000 and PH1000,
- certain oils of the SF series from the company General Electric, such as SF 1023, SF 1154, SF 1250 and SF 1265.

The silicone gums that may be present in the composition according to the invention are especially polydiorganosiloxanes having high number-average molecular masses of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Mention may be made more particularly of the following products:
- polydimethylsiloxane gums,
- polydimethylsiloxane/methylvinylsiloxane gums,
- polydimethylsiloxane/diphenylsiloxane gums,
- polydimethylsiloxane/phenylmethylsiloxane gums,
  - polydimethylsiloxane/diphenylsiloxane/methylvinylsiloxane gums.

Products that may be used more particularly are the following mixtures:
- mixtures formed from a polydimethylsiloxane hydroxylated at the end of the chain (known as dimethiconol according to the nomenclature of the CTFA dictionary) and from a cyclic polydimethylsiloxane (known as cyclomethicone according to the nomenclature of the CTFA dictionary), such as the product Q2 1401 sold by the company Dow Corning,
- mixtures formed from a polydimethylsiloxane gum with a cyclic silicone, such as the product SF 1214 Silicone Fluid from the company General Electric, this product being an SF 30 gum corresponding to a dimethicone, having a number-average molecular weight of 500 000, dissolved in the oil SF 1202 Silicone Fluid corresponding to decamethylcyclopentasiloxane, mixtures of two PDMSs with different viscosities, and more particularly of a PDMS gum and a PDMS oil, such as the product SF 1236 from the company General Electric. The product SF 1236 is a mixture of a gum SE 30 defined above, with a viscosity of 20 m²/s and of an oil SF 96 with a viscosity of 5×10⁻⁶ m²/s. This product preferably comprises 15% of gum SE 30 and 85% of an oil SF 96.

The organopolysiloxane resins that may be present in the composition according to the invention are crosslinked siloxane systems containing the following units: $R_2SiO_{2/2}$, $R_3SiO_{1/2}$, $RSiO_{3/2}$ and $SiO_{4/2}$ in which R represents a hydrocarbon group containing 1 to 16 carbon atoms or a phenyl group. Among these products, the ones that are particularly preferred are those in which R denotes a $C_1$-$C_4$ alkyl group, more particularly methyl, or a phenyl group.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the trimethyl siloxysilicate type resins sold in particular under the names X22-4914, X21-5034 and X21-5037 by the company Shin-Etsu.

The organomodified silicones that may be present in the composition according to the invention are silicones as defined above and comprising in their structure one or more organofunctional groups attached via a hydrocarbon-based group.

Among the organomodified silicones, mention may be made of polyorganosiloxanes comprising:
  polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet L 722, L 7500, L 77 and L 711 by the company Union Carbide, and the ($C_{12}$)alkylmethicone copolyol sold by the company Dow Corning under the name Q2 5200,
  thiol groups, such as the products sold under the names GP 72 A and GP 71 from the company Genesee,
  alkoxylated groups, such as the product sold under the name Silicone Copolymer F-755 by SWS Silicones and Abil Wax 2428, 2434 and 2440 by the company Goldschmidt,
  hydroxylated groups, such as the polyorganosiloxanes containing a hydroxyalkyl function, described in French patent application FR 2 589 476,
  acyloxyalkyl groups, for instance the polyorganosiloxanes described in U.S. Pat. No. 4,957,732,
  anionic groups of the carboxylic acid type, for instance in the products described in patent EP 186 507 from the company Chisso Corporation, or of the alkylcarboxylic type, such as those present in the product X-22-3701E from the company Shin-Etsu; 2-hydroxyalkyl sulfonate; 2-hydroxyalkyl thiosulphate such as the products sold by the company Goldschmidt under the names Abil S201 and Abil S255.

According to the invention, silicones comprising a polysiloxane portion and a non-silicone organic chain portion, one of the two portions constituting the main chain of the polymer and the other being grafted onto the said main chain, can also be used. These polymers are described, for example, in patent applications EP-A-412,704, ep-a-412,707, ep-a-640,105 and WO95/00578, ep-a-582,152 and WO93/23009 and U.S. Pat. Nos. 4,693,935, 4,728,571 and 4,972,037, the disclosures of which are specifically incorporated by reference herein. These polymers are preferably anionic or non-ionic.

Such polymers are, for example, copolymers, which may be obtained by radical polymerization from a monomer mixture comprising:
  a) 50 to 90% by weight of tert-butyl acrylate;
  b) 0 to 40% by weight of acrylic acid; 5 to 40% by weight of silicone macromer of formula:
wherein,
V is a number ranging from 5 to 700; the weight percentages being calculated relative to the total weight of the monomers.

Other examples of grafted silicone polymers are, in particular, polydimethylsiloxane (PDMSs) onto which are grafted, via a connecting chain of thiopropylene type, mixed polymer units of the poly(meth)acrylic acid type and of the polyalkyl(methyl)acrylate type and polydimethylsiloxanes (PDMSs) on which are grafted, via a connecting chain of thiopropylene type, polymer units of the polyisobutyl(meth) acrylate type.

Preferably, the non amino silicones are chosen from polyalkylsiloxanes, and more preferentially from polydimethylsiloxanes.

The non-amino silicones, which are preferably used in the present invention have a viscosity equals to 60 000 cst at 25° C. and shear rate 1 s⁻¹.

The viscosity may be measured at 25° C. with viscosimeters or rheometers preferably with cone-plan geometry.

The silicones used in the composition of the invention may also be chosen from amino silicones.

For the purposes of the present invention, the term "amino silicone" means any silicone comprising at least one primary, secondary or tertiary amine function or a quaternary ammonium group.

The amino silicones that may be used in the cosmetic composition according to the present invention are chosen from:
  (a) the compounds corresponding to formula (XVIII) below:

$$(R_1)_a(T)_{3-a}Si[OSi(T)_2]_n[OSi(T)_b(R_1)_{2-b}]_mOSi(T)_{3-a}(R_1)_a \quad (XVIII)$$

wherein,
  T is a hydrogen atom or a phenyl, hydroxyl (—OH) or $C_1$-$C_8$ alkyl group, and preferably methyl, or a $C_1$-$C_8$ alkoxy, preferably methoxy,
  a denotes the number 0 or an integer from 1 to 3, and preferably 0,
  b denotes 0 or 1, and in particular 1,
  m and n are numbers such that the sum (n+m) can range especially from 1 to 2000 and in particular from 50 to 150, it being possible for n to denote a number from 0 to 1999 and in particular from 49 to 149, and for m to denote a number from 1 to 2000 and in particular from 1 to 10, and
  $R_1$ is a monovalent group of formula —$C_qH_{2q}$L in which q is a number from 2 to 8 and L is an optionally quaternized amino group chosen from the following groups:

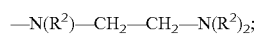

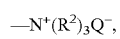

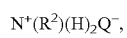

$N(R^2)_2HQ^-$, $-N(R^2)-CH_2-CH_2-N^+(R^2)(H)_2Q^-$, wherein, $R^2$ may denote a hydrogen atom, a phenyl, a benzyl or a saturated monovalent hydrocarbon-based group, for example a $C_1$-$C_{20}$ alkyl group, and $Q^-$ represents a halide ion, for instance fluoride, chloride, bromide or iodide.

In particular, the amino silicones corresponding to the definition of formula (XVIII) are chosen from the compounds corresponding to formula (XIX) below:

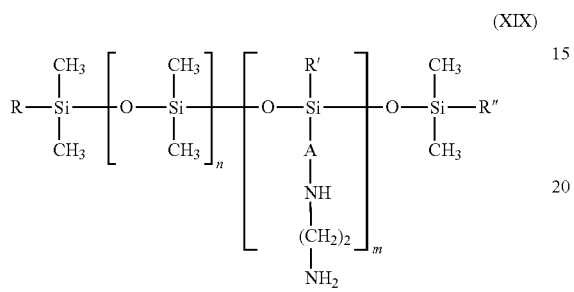

(XIX)

wherein, R, R' and R", which may be identical or different, denote a $C_1$-$C_4$ alkyl group, preferably $CH_3$; a $C_1$-$C_4$ alkoxy group, preferably methoxy; or OH; A represents a linear or branched, $C_3$-$C_8$ and preferably $C_3$-$C_6$ alkylene group; m and n are integers dependent on the molecular weight and whose sum is between 1 and 2000.

According to a first possibility, R, R' and R", which may be identical or different, represent a $C_1$-$C_4$ alkyl or hydroxyl group, A represents a $C_3$ alkylene group and m and n are such that the weight-average molecular mass of the compound is between 5000 and 500 000 approximately. Compounds of this type are referred to in the CTFA dictionary as "amodimethicones".

According to a second possibility, R, R' and R", which may be identical or different, each represent a $C_1$-$C_4$ alkoxy or hydroxyl group, at least one of the groups R or R" is an alkoxy group and A represents a $C_3$ alkylene group. The hydroxy/alkoxy mole ratio is preferably between 0.2/1 and 0.4/1 and advantageously equal to 0.3/1. Moreover, m and n are such that the weight-average molecular mass of the compound is between 2000 and $10^6$. More particularly, n is between 0 and 999 and m is between 1 and 1000, the sum of n and m being between 1 and 1000.

In this category of compounds, mention may be made, inter alia, of the product Belsil® ADM 652 sold by the company Wacker.

According to a third possibility, R and R", which are different, each represent a $C_1$-$C_4$ alkoxy or hydroxyl group, at least one of the groups R or R" being an alkoxy group, R' representing a methyl group and A representing a $C_3$ alkylene group. The hydroxy/alkoxy mole ratio is preferably between 1/0.8 and 1/1.1 and advantageously equal to 1/0.95. Moreover, m and n are such that the weight-average molecular mass of the compound is between 2000 and 200 000. More particularly, n is between 0 and 999 and m is between 1 and 1000, the sum of n and m being between 1 and 1000.

More particularly, mention may be made of the product Fluid WR® 1300 sold by the company Wacker.

Note that the molecular mass of these silicones is determined by gel permeation chromatography (ambient temperature, polystyrene standard; μ styragem columns; eluent THF; flow rate 1 mm/minute; 200 μl of a solution containing 0.5% by weight of silicone in THF are injected, and detection is performed by refractometry and UV-metry).

A product corresponding to the definition of formula (XIX) is in particular the polymer known in the CTFA dictionary as Trimethylsilyl Amodimethicone, corresponding to formula (XX) below:

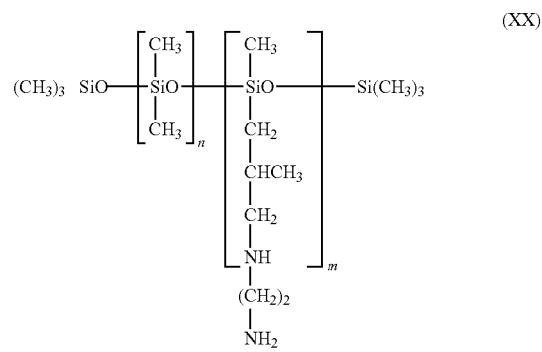

(XX)

wherein, n and m have the meanings given above in accordance with formula (XVIII).

Such compounds are described, for example, in patent EP 95238. A compound of formula (XX) is sold, for example, under the name Q2-8220 by the company OSI.

(b) the compounds corresponding to formula (XXI) below:

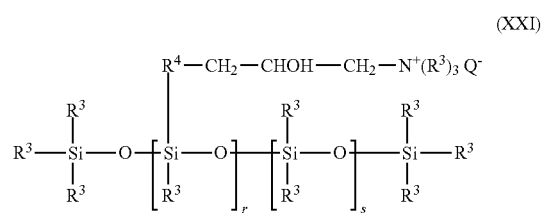

(XXI)

wherein, $R^3$ represents a $C_1$-$C_{18}$ monovalent hydrocarbon-based group, and in particular a $C_1$-$C_{18}$ alkyl or $C_2$-$C_{18}$ alkenyl group, for example methyl, $R^4$ represents a divalent hydrocarbon-based group, especially a $C_1$-$C_{18}$ alkylene group or a divalent $C_1$-$C_{18}$, and for example $C_1$-$C_8$, alkylenoxy group, $Q^-$ is a halide ion, in particular chloride;

r represents a mean statistical value from 2 to 20 and in particular from 2 to 8, and s represents a mean statistical value from 20 to 200 and in particular from 20 to 50.

Such compounds are described more particularly in U.S. Pat. No. 4,185,087.

A compound falling within this class is the product sold by the company Union Carbide under the name Ucar Silicone ALE 56.

(c) quaternary ammonium silicones especially of formula (XXII):

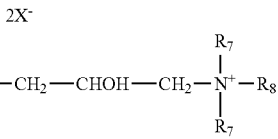

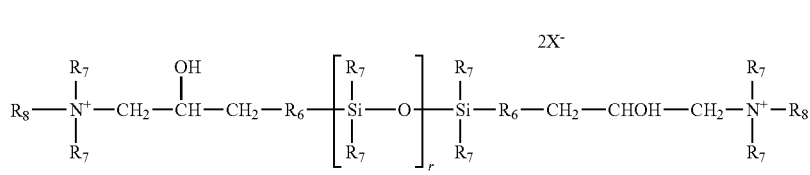

wherein,
- $R_7$, which may be identical or different, represent a monovalent hydrocarbon-based group containing from 1 to 18 carbon atoms, and in particular a $C_1$-$C_{18}$ alkyl group, a $C_2$-$C_{18}$ alkenyl group or a ring comprising 5 or 6 carbon atoms, for example methyl,
- $R_6$ represents a divalent hydrocarbon-based group, especially a $C_1$-$C_{18}$ alkylene group or a divalent $C_1$-$C_{18}$, and for example $C_1$-$C_8$, alkylenoxy group linked to the Si via an SiC bond,
- $R_8$, which may be identical or different, represent a hydrogen atom, a monovalent hydrocarbon-based group containing from 1 to 18 carbon atoms, and in particular a $C_1$-$C_{18}$ alkyl group, a $C_2$-$C_{18}$ alkenyl group or a group —$R_6$—$NHCOR_7$;
- $X^-$ is an anion such as a halide ion, especially chloride, or an organic acid salt (acetate, etc.); and
- r represents a mean statistical value from 2 to 200 and in particular from 5 to 100.

These silicones are described, for example, in patent application EP-A-0 530 974.

d) the amino silicones of formula (XXIII) below:

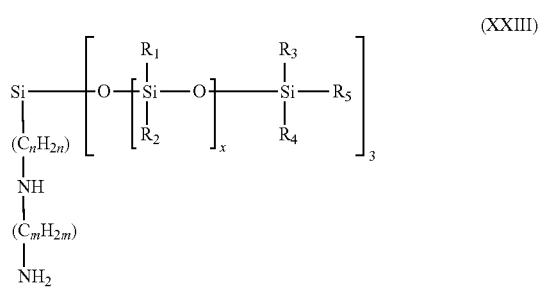

wherein,
- $R_1$, $R_2$, $R_3$ and $R_4$, which may be identical or different, denote a $C_1$-$C_4$ alkyl group or a phenyl group,
- $R_5$ denotes a $C_1$-$C_4$ alkyl group or a hydroxyl group,
- n is an integer ranging from 1 to 5,
- m is an integer ranging from 1 to 5, and
- x is chosen such that the amine number is between 0.01 and 1 meq/g.

When these compounds are used, one particularly advantageous embodiment involves their combined use with cationic and/or nonionic surfactants.

By way of example, use may be made of the product sold under the name Cationic Emulsion DC939 by the company Dow Corning, a cationic surfactant, namely trimethylcetylammonium chloride and a nonionic surfactant of formula $C_{13}H_{27}$—$(OC_2H_4)_{12}$—OH, known under the CTFA name Trideceth-12.

Another commercial product that may be used according to the invention is the product sold under the name Dow Corning Q2 7224 by the company Dow Corning, comprising, in combination, trimethylsilyl amodimethicone of formula (XX) described above, a nonionic surfactant of formula $C_8H_{17}$—$C_6H_4$—$(OCH_2CH_2)_{40}$—OH, known under the CTFA name Octoxynol-40, a second nonionic surfactant of formula $C_{12}H_{25}$—$(OCH_2$—$CH_2)_6$—OH, known under the CTFA name Isolaureth-6, and propylene glycol.

The silicones of the invention may also be silicones grafted with anionic groups, such as the compounds VS 80 or VS 70 sold by the company 3M.

Preferentially, the amino silicones used in the present invention are the products sold under the names DC 8194, DC 8299, DC 1689, DC 5-7113, DC 8500, DC 8566, DC8170 and DC 8401 by the company Dow Corning.

According to the invention, the silicones can be used in the form of emulsions.

Preferably, the silicones are used in the form of emulsions having an average particle size ranging from 50 nm to 10 µm, more preferably from 100 nm to 2 µm, and even more preferably from 100 to 500 nm. Indeed, silicone deposition remains high, irrespective to the molecular weight, when the average particle size is preferably ranging from 100 nm to 2 µm.

According to a preferred embodiment of the invention, the composition contains one or more non-amino silicone and one or more amino silicone, preferably one or more polyalkylsiloxane and one or more amodimethicone, even more preferably one or more polydimethylsiloxane and one or more amodimethicone.

In this embodiment, the non-amino silicone and the amino silicone are both preferably present in the composition in the form of emulsions as described above. In a particularly preferred embodiment, the non-amino silicone and the amino silicone are present as one emulsion comprising both types of silicones. Preferably, the emulsion has an average particle size of from 100 nm to 2000 nm, more preferably from 100 nm to 500 nm, more preferably form 150 nm to 350 nm. The average particle size is expressed in volume (D50 average particle size).

The total amount of silicone(s) advantageously ranges from 0.5 to 15% by weight, more preferentially from 1 to 10% by weight, and even more preferably from 1.5 to 5% by weight relative to the total weight of the composition.

Cationic Polymers

The composition of the invention further comprises one or more cationic polymers.

The term "cationic polymer" means any polymer containing cationic groups and/or groups that can be ionized to cationic groups, which are preferably non-siliceous.

The cationic polymers that may be used in accordance with the present invention may be chosen from any of those already known per se for styling the hair, namely, especially, those described in patent application EP-A-0 337 354 and in French patent applications FR-A-2 270 846, 2 383 660, 2 598 611, 2 470 596 and 2 519 863.

The preferred cationic polymers that may be used in the composition according to the invention are chosen from those containing units comprising primary, secondary, tertiary and/or quaternary amine groups that may either form part of the main polymer chain or may be borne by a side substituent directly connected thereto.

The cationic polymers preferably have a weight-average molecular mass of greater than $10^5$, preferably greater than $10^6$ and more preferably of between $10^6$ and $10^8$.

Among the cationic polymers that may be used in accordance with the invention, mention may be made more particularly of polymers of polyamine, polyaminoamide and polyquaternary ammonium type.

The polymers of polyamine, polyaminoamide and polyquaternary ammonium type that may be used in the composition according to the present invention are especially those described in French patents 2 505 348 and 2 542 997.

Among these polymers, mention may be made especially of:

(1) homopolymers or copolymers derived from acrylic or methacrylic esters or amides and comprising at least one of the units of formulae (VIII), (IX), (X) and (XI) below:

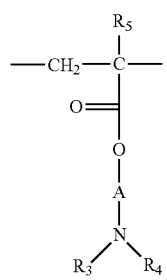
(VIII)

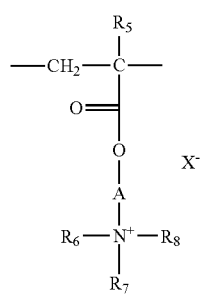
(IX)

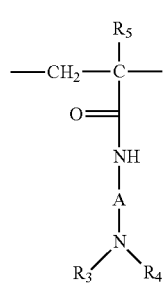
(X)

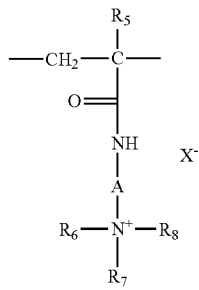
(XI)

wherein,
$R_3$ and $R_4$, which may be identical or different, represent a hydrogen atom or an alkyl group containing from 1 to 6 carbon atoms, and preferably a methyl or ethyl group, $R_5$, which may be identical or different, denote a hydrogen atom or a $CH_3$ group, A, which may be identical or different, represent a linear or branched alkyl group of 1 to 6 carbon atoms, preferably 2 or 3 carbon atoms, or a hydroxyalkyl group comprising 1 to 4 carbon atoms, $R_6$, $R_7$ and $R_8$, which may be identical or different, represent an alkyl group containing from 1 to 18 carbon atoms or a benzyl group, and preferably an alkyl group containing from 1 to 6 carbon atoms, and $X^-$ denotes an anion derived from a mineral or organic acid, preferably a methosulfate anion or a halide, and better still a chloride or bromide.

The copolymers of family (1) may also contain one or more units derived from comonomers which may be chosen from the family of acrylamides, methacrylamides, diacetone acrylamides, acrylamides and methacrylamides substituted on the nitrogen atom with lower ($C_1$-$C_4$) alkyls, acrylic or methacrylic acids or esters thereof, vinyllactams such as vinylpyrrolidone or vinylcaprolactam, and vinyl esters.

Thus, among these copolymers of the family (1), mention may be made of:

copolymers of acrylamide and of dimethylaminoethyl methacrylate quaternized with dimethyl sulfate or with a dimethyl halide, such as the product sold under the name Hercofloc by the company Hercules, copolymers of acrylamide and of methacryloyloxyethyltrimethylammonium chloride, described, for example, in patent application EP-A-080 976 and sold under the name Bina Quat P 100 by Ciba-Geigy, the copolymer of acrylamide and of methacryloyloxyethyltrimethylammonium methosulfate sold under the name Reten by the company Hercules, quaternized or non-quaternized vinylpyrrolidone/dialkylaminoalkyl acrylate or methacrylate copolymers, such as the products sold under the name Gafquat by the company ISP, such as, for example, Gafquat 734 or Gafquat 755, or alternatively the products known as Copolymer 845, 958 and 937. These polymers are described in detail in French patents 2 077 143 and 2 393 573, dimethylamino ethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, quaternized vinylpyrrolidone/dimethylaminopropylmethacrylamide copolymers such as the product sold under the name Gafquat HS 100 by the company ISP, and crosslinked polymers of methacryloyloxy($C_1$-$C_4$)alkyltri ($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, in particular methylenebisacrylamide. Use may be made more particularly of a crosslinked acrylamide/methacryloyloxyethyltrimethylammonium chloride copolymer (20/80 by weight) in the form of a dispersion containing 50% by weight of the said copolymer in mineral oil. This dispersion is sold under the name Salcare® SC 92 by the company Ciba. Use may also be made of a crosslinked methacryloyloxyethyltrimethylammonium chloride homopolymer (INCI name Polyquaternium-37), for example the polymer sold under the name Cosmedia Ultragel 300 by the company Cognis; or as a dispersion in mineral oil or in a liquid ester; these dispersions are sold under the names Salcare® SC 95 and Salcare® SC 96 by the company Ciba.

(2) polymers formed from piperazinyl units and divalent alkylene or hydroxyalkylene radicals containing straight or branched chains, optionally interrupted with oxygen, sulfur or nitrogen atoms or with aromatic or heterocyclic rings, and also the oxidation and/or quaternization products of these polymers. Such polymers are especially described in French patents 2 162 025 and 2 280 361.

(3) water-soluble polyamino amides prepared in particular by polycondensation of an acidic compound with a polyamine. These polyaminoamides may be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative, the crosslinking agent being used in proportions ranging from 0.025 to 0.35 mol per amine group of the polyaminoamide. These polyaminoamides can be alkylated or, if they comprise one or more tertiary amine functions, they can be quaternized. Such polymers are especially described in French patents 2 252 840 and 2 368 508.

(4) Polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl group comprises from 1 to 4 carbon atoms and preferably denotes methyl, ethyl or propyl. Such polymers are especially described in French patent 1 583 363.

Among these derivatives, mention may be made more particularly of the adipic acid/dimethylaminohydroxypropyl/diethylenetriamine polymers sold under the name Cartaretine F, F4 or F8 by the company Sandoz.

(5) The polymers obtained by reaction of a polyalkylene polyamine comprising two primary amine groups and at least one secondary amine group with a dicarboxylic acid chosen from diglycolic acid and saturated aliphatic dicarboxylic acids having from 3 to 8 carbon atoms. The mole ratio between the polyalkylene polyamine and the dicarboxylic acid is between 0.8:1 and 1.4:1; the polyamino amide resulting therefrom is reacted with epichlorohydrin in a mole ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name Hercosett 57 by the company Hercules Inc. or alternatively under the name PD 170 or Delsette 101 by the company Hercules in the case of the adipic acid/epoxypropyl-diethylenetriamine copolymer.

(6) Cyclopolymers of alkyldiallylamine or of dialkyldiallylammonium, such as the homopolymers or copolymers comprising, as main constituent of the chain, units corresponding to formula (XII) or (XIII):

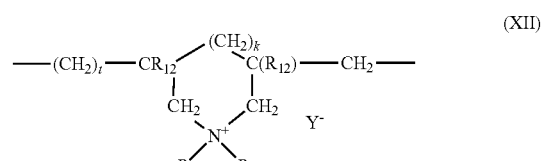

(XII)

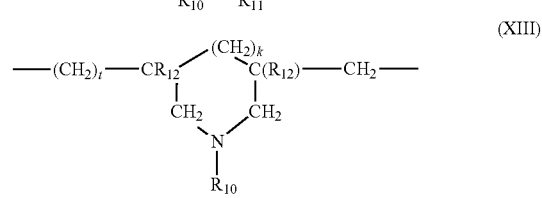

(XIII)

wherein, k and t are equal to 0 or 1, the sum k+t being equal to 1; $R_{12}$ denotes a hydrogen atom or a methyl group; $R_{10}$ and $R_{11}$, independently of each other, denote an alkyl group containing from 1 to 6 carbon atoms, a hydroxyalkyl group in which the alkyl group preferably contains 1 to 5 carbon atoms, a lower ($C_1$-$C_4$) amidoalkyl group, or $R_{10}$ and $R_{11}$ may denote, together with the nitrogen atom to which they are attached, heterocyclic groups such as piperidyl or morpholinyl; $Y^-$ is an anion such as bromide, chloride, acetate, borate, citrate, tartrate, bisulfate, bisulfite, sulfate or phosphate. These polymers are in particular described in French patent 2 080 759 and in its Certificate of Addition 2 190 406.

$R_{10}$ and $R_{11}$, independently of each other, preferably denote an alkyl group having from 1 to 4 carbon atoms.

Among the polymers defined above, mention may be made more particularly of the dimethyldiallylammonium chloride homopolymer sold under the name Merquat 100 by the company Nalco and its homologues of low weight-average molecular weights, and the copolymers of diallyldimethylammonium chloride and of acrylamide sold under the name Merquat 550.

(7) The quaternary diammonium polymer in particular containing repeating units corresponding to the formula (XIV):

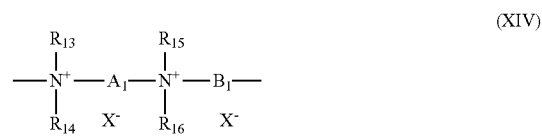

(XIV)

wherein,

R$_{13}$, R$_{14}$, R$_{15}$ and R$_{16}$, which may be identical or different, represent aliphatic, alicyclic or arylaliphatic groups containing from 1 to 20 carbon atoms or lower hydroxyalkylaliphatic radicals, or alternatively R$_{13}$, R$_{14}$, R$_{15}$ and R$_{16}$, together or separately, constitute, with the nitrogen atoms to which they are attached, heterocycles optionally containing a second heteroatom other than nitrogen, or alternatively R$_{13}$, R$_{14}$, R$_{15}$ and R$_{16}$, represent a linear or branched C$_1$-C$_6$ alkyl group substituted with a nitrile, ester, acyl or amide group or a group COOR$_{17}$D or CONHR$_{17}$D where R$_{17}$ is an alkylene and D is a quaternary ammonium group, A$_1$ and B$_1$ represent polymethylene groups containing from 2 to 20 carbon atoms which may be linear or branched, and saturated or unsaturated, and which may contain, linked to or inserted in the main chain, one or more aromatic rings, or one or more oxygen or sulfur atoms or sulfoxide, sulfone, disulfide, amino, alkylamino, hydroxyl, quaternary ammonium, ureido, amide or ester groups, and X$^-$ denotes an anion derived from a mineral or organic acid.

A$_1$, R$_{13}$ and R$_{15}$ can form, with the two nitrogen atoms to which they are attached, a piperazine ring.

In addition, if A$_1$ denotes a linear or branched, saturated or unsaturated alkylene or hydroxyalkylene radical, B$_1$ may also denote a group (CH$_2$)$_n$—CO—D—OC—(CH$_2$)$_p$—, n and p are integers ranging from 2 to 20 approximately, in which D denotes:

a) a glycol residue of formula: —O—Z—O—, where Z denotes a linear or branched hydrocarbon-based radical or a group corresponding to one of the following formulae:

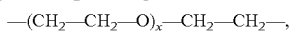

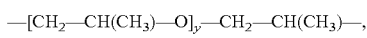

in which x and y denote an integer from 1 to 4, representing a defined and unique degree of polymerization or any number from 1 to 4 representing an average degree of polymerization, b) a bis-secondary diamine residue such as a piperazine derivative, c) a bis-primary diamine residue of formula: —NH—Y—NH—, where Y denotes a linear or branched hydrocarbon-based radical, or else the divalent radical —CH$_2$—CH$_2$—S—S—CH$_2$—CH$_2$—, d) a ureylene group of formula —NH—CO—NH—.

Preferably, X$^-$ is an anion such as chloride or bromide.

These polymers have a number-average molecular mass generally of between 1000 and 100 000.

Polymers of this type are especially described in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may more particularly be made of polymers that are formed from repeating units corresponding to formula (XV):

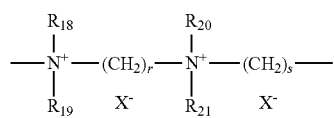

wherein, R$_{18}$, R$_{19}$, R$_{20}$ and R$_{21}$, which may be identical or different, denote an alkyl or hydroxyalkyl group containing from 1 to 4 carbon atoms approximately, r and s are integers ranging from 2 to 20 approximately, and X$^-$ is an anion derived from a mineral or organic acid.

A compound of formula (XV) that is particularly preferred is that for which R$_{18}$, R$_{19}$, R$_{20}$ and R$_{21}$ represent a methyl radical and r=3, s=6 and X=Cl, called hexadimethrine chloride in INCI nomenclature (CTFA).

(8) Polyquaternary ammonium polymers formed especially from units of formula (XVI):

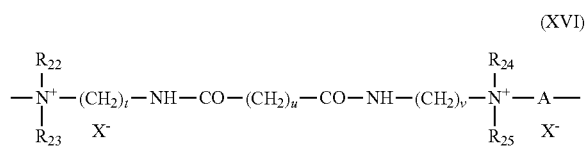

wherein,

R$_{22}$, R$_{23}$, R$_{24}$ and R$_{25}$, which may be identical or different, represent a hydrogen atom or a methyl, ethyl, propyl, β-hydroxyethyl, β-hydroxypropyl or —CH$_2$CH$_2$(OCH$_2$CH$_2$)$_p$OH group, where p is equal to 0 or to an integer between 1 and 6, with the proviso that R$_{22}$, R$_{23}$, R$_{24}$ and R$_{25}$ do not simultaneously represent a hydrogen atom, t and u, which may be identical or different, are integers between 1 and 6, v is equal to 0 or to an integer between 1 and 34, X$^-$ denotes an anion such as a halide, and A denotes a dihalide radical or preferably represents —CH$_2$—CH$_2$—O—CH$_2$—CH$_2$—.

Such compounds are especially described in patent application EP-A-122 324.

Among these, mention may be made, for example, of the products Mirapol® A 15, Mirapol® AD1, Mirapol® AZ1 and Mirapol® 175, sold by the company Miranol.

(9) Quaternary polymers of vinylpyrrolidone and/or of vinylimidazole, for instance the products sold under the names Luviquat® FC 905, FC 550 and FC 370 and Luviquat Excellence by the company BASF.

(10) Cationic polysaccharides, preferably cationic celluloses and galactomannan gums.

Among cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are described in French patent 1 492 597. These polymers are also defined in the CTFA dictionary as quaternary ammoniums of hydroxyethylcellulose that have reacted with an epoxide substituted with a trimethylammonium group.

The cationic cellulose copolymers or the cellulose derivatives grafted with a water-soluble quaternary ammonium monomer are described especially in U.S. Pat. No. 4,131,576, such as hydroxyalkyl celluloses, for instance hydroxymethyl, hydroxyethyl or hydroxypropyl celluloses grafted especially with a methacryloylethyltrimethylammonium, methacrylamidopropyltrimethylammonium or dimethyldiallylammonium salt.

A cationic cellulose copolymer that may especially be mentioned is Polyquaternium-4, which is a copolymer of hydroxyethylcellulose and of diallyldimethylammonium chloride.

Mention may also be made of associative celluloses such as alkylhydroxyethylcelluloses quaternized with $C_8$-$C_{30}$ fatty chains, such as the product Quatrisoft LM 200®, sold by the company Amerchol/Dow Chemical (INCI name Polyquaternium-24) and the products Crodacel QM® (INCI name PG-Hydroxyethylcellulose cocodimonium chloride), Crodacel QL® ($C_{12}$ alkyl) (INCI name PG-Hydroxyethylcellulo se lauryldimonium chloride) and Crodacel QS® ($C_{18}$ alkyl) (INCI name PG-Hydroxyethylcellulose stearyldimonium chloride) sold by the company Croda.

Mention may also be made of other fatty-chain hydroxyethylcellulose derivatives such as the commercial products Softcat Polymer SL® such as SL-100, SL-60, SL-30 and SL-5 from the company Amerchol/Dow chemical of INCI name Polyquaternium-67.

The cationic galactomannan gums are described more particularly in U.S. Pat. No. 3,589,578 and 4 031 307, in particular guar gums containing cationic trialkylammonium groups. Guar gums modified with a salt such as 2,3-epoxypropyltrimethylammonium chloride are used, for example.

(11) Cationic proteins or cationic protein hydrolysates, polyalkyleneimines, in particular polyethyleneimines, polymers containing vinylpyridine or vinylpyridinium units, condensates of polyamines and of epichlorohydrin, quaternary polyureylenes and chitin derivatives.

The cationic proteins or protein hydrolysates are, in particular, chemically modified polypeptides bearing quaternary ammonium groups at the end of the chain, or grafted thereon. Their molecular mass may vary, for example, from 1500 to 10 000 and in particular from 2000 to 5000 approximately. Among these compounds, mention may be made especially of:

collagen hydrolysates bearing triethylammonium groups, such as the products sold under the name Quat-Pro E by the company Maybrook and referred to in the CTFA dictionary as Triethonium Hydrolyzed Collagen Ethosulfate, collagen hydrolysates bearing trimethylammonium chloride and trimethylstearylammonium chloride groups, which are sold under the name Quat-Pro S by the company Maybrook and are referred to in the CTFA dictionary as Steartrimonium Hydrolyzed Collagen, animal protein hydrolysates bearing trimethylbenzylammonium groups, such as the products sold under the name Crotein BTA by the company Croda and referred to in the CTFA dictionary as Benzyltrimonium hydrolyzed animal protein, protein hydrolysates bearing quaternary ammonium groups on the polypeptide chain, the said ammonium groups comprising at least one alkyl radical having from 1 to 18 carbon atoms.

Among these protein hydrolysates, mention may be made, inter alia, of:

Croquat L, in which the quaternary ammonium groups comprise a $C_{12}$ alkyl group, Croquat M, in which the quaternary ammonium groups comprise $C_{10}$-$C_{18}$ alkyl groups, Croquat S, in which the quaternary ammonium groups comprise a $C_{18}$ alkyl group, Crotein Q, in which the quaternary ammonium groups comprise at least one alkyl group having from 1 to 18 carbon atoms.

These various products are sold by the company Croda.

Other quaternized proteins or hydrolysates are, for example, those corresponding to the formula (XVII):

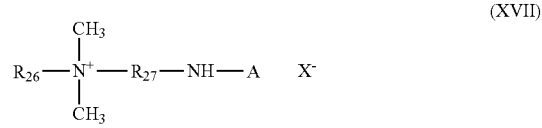

(XVII)

wherein, $X^-$ is an anion of an organic or mineral acid, A denotes a protein residue derived from collagen protein hydrolysates, $R_{26}$ denotes a lipophilic group comprising up to 30 carbon atoms, $R_{27}$ represents an alkylene group having 1 to 6 carbon atoms. Mention may be made, for example, of the products sold by the company Inolex, under the name Lexein QX 3000, referred to in the CTFA dictionary as Cocotrimonium Collagen Hydrolysate.

Mention may also be made of quaternized plant proteins such as wheat, corn or soybean proteins, for instance quaternized wheat proteins. Mention may be made of those sold by the company Croda under the names Hydrotriticum WQ or QM, referred to in the CTFA dictionary as Cocodimonium hydrolysed wheat protein, Hydrotriticum QL, referred to in the CTFA dictionary as Laurdimonium hydrolysed wheat protein, or else Hydrotriticum QS, referred to in the CTFA dictionary as Steardimonium hydrolysed wheat protein.

(12) Polyamines such as Polyquart R H sold by Cognis, referred to under the name polyethylene glycol (15) tallow polyamine in the CTFA dictionary.

(13) Polymers comprising in their structure:

(a) one or more units corresponding to formula (A) below:

(A)

(b) optionally one or more units corresponding to formula (B) below:

(B)

In other words, these polymers may be chosen in particular from homopolymers or copolymers comprising one or more units derived from vinylamine and optionally one or more units derived from vinylformamide.

Preferably, these cationic polymers are chosen from polymers comprising, in their structure, from 5 mol % to 100 mol % of units corresponding to formula (A) and from 0 to 95 mol % of units corresponding to formula (B), preferentially from 10 mol % to 100 mol % of units corresponding to formula (A) and from 0 to 90 mol % of units corresponding to formula (B).

These polymers may be obtained, for example, by partial hydrolysis of polyvinylformamide.

This hydrolysis may be performed in an acidic or basic medium.

The weight-average molecular mass of the said polymer, measured by light scattering, may range from 1000 to 3 000 000 g/mol, preferably from 10 000 to 1 000 000 g/mol and more particularly from 100 000 to 500 000 g/mol.

The cationic charge density of these polymers can vary from 2 to 20 meq/g, preferably from 2.5 to 15 meq/g and more particularly from 3.5 to 10 meq/g.

The polymers comprising units of formula (A) and optionally units of formula (B) are sold especially under the name Lupamin by the company BASF, for instance, and in a non-limiting manner, the products sold under the names Lupamin 9095, Lupamin 5095, Lupamin 1095, Lupamin 9030 and Lupamin 9010.

Preferably, the composition of the invention contains one or more cationic polymer belonging to family (10) above, and in particular one or more cationic galactomannan gum such as guar gums containing cationic trialkylammonium groups.

The amount of cationic polymer(s) advantageously ranges from 0.01 to 10% by weight, more preferably from 0.05 to 5% by weight, and most preferably from 0.1 to 2% by weight, with regard to the total weight of the composition.

Fatty Alcohols

The composition, according to the present invention, further comprises one or more fatty alcohols.

For the purposes of the present invention, the term "fatty alcohol" means any saturated or unsaturated, linear or branched alcohol comprising at least 8 carbon atoms and which is not oxyalkylenated.

Preferably, the fatty alcohols are solid at room temperature (25° C.) and at atmospheric pressure (1.013*10$^5$ Pa). The fatty alcohols are preferably chosen from the compounds of general formula (I)

$$R\text{—}OH \qquad (I)$$

wherein R denotes a saturated or unsaturated, linear or branched radical containing from 8 to 30, preferably from 10 to 30 carbon atoms, more preferentially from 12 to 22 carbon atoms, and better still from 16 to 22 carbon atoms.

R preferably denotes a linear or branched $C_8$-$C_{30}$, more preferentially $C_{16}$-$C_{22}$ alkyl or a linear or branched $C_8$-$C_{30}$, more preferentially $C_{16}$-$C_{22}$ alkenyl group, and better still linear. R may be substituted with one or more hydroxyl groups.

Examples of fatty alcohols that may be mentioned include cetyl alcohol, stearyl alcohol, oleyl alcohol, behenyl alcohol, linoleyl alcohol, palmitoleyl alcohol, arachidonyl alcohol and erucyl alcohol, and mixtures thereof.

The fatty alcohol may represent a mixture of fatty alcohols, which means that several species of fatty alcohol may coexist, in the form of a mixture, in a commercial product.

Fatty alcohol mixtures that may be mentioned include cetylstearyl (or cetearyl) alcohol.

Among all the fatty alcohols that may be used according to the invention, use is preferably made of one or more fatty alcohols chosen from cetyl alcohol, stearyl alcohol, and mixtures thereof such as cetearyl alcohol.

The amount of fatty alcohols, in the composition of the present invention, advantageously ranges from 0.05 to 15% by weight, preferably from 0.1 to 10% by weight, and more preferentially from 0.5 to 5% by weight, relative to the total weight of the composition.

Clays:

The composition according to the invention comprises at least one clay.

Clays are products which are already well known per se and which are described, for example, in the publication "Minéralogie des argiles" [Mineralogy of Clays], S. Caillère, S. Hénin and M. Rautureau, 2nd Edition 1982, Masson, the teaching of which is included herein by way of reference.

Mention may be made, among clays, as examples, of clays of the family of the smectites, such as laponite and montmorillonite, of the family of the kaolinites, such as kaolinite, dickite or nacrite, optionally modified clays of the family of halloysite, donbassite, antigorite, berthierine or pyrophyllite, montmorillonites, beidellite, vermiculites, talc, stevensite, hectorites, bentonites, saponites, chlorites, sepiolite and illite.

The clay or clays present in the composition of the invention can be natural or synthetic. Natural clay is a sedimentary rock in large part composed of specific minerals, silicates, generally, of aluminum. Kaolin is thus natural clay comprising kaolinite.

Clays can also be chemically modified by various compounds, such as acrylic acids, polysaccharides (for example carboxymethylcellulose) or organic cations.

Use is preferably made, in the context of the present invention, of clays which are cosmetically compatible with and acceptable to the hair, skin and/or scalp.

According to a specific embodiment of the present invention, the clays employed are chosen from kaolinites, montmorillonites, saponites, laponites, bentonites, and in particular hectorites, and illites. Use will more particularly be made of mixtures of clays, and natural clays.

Mention may be made, as natural clay, of green clays, in particular rich in illite; clays rich in montmorillonite, known under the name of fuller's earth, or such as bentonites, or also white clays rich in kaolinite.

Mention may in particular be made, as bentonites, of those sold under the names "Bentone 38 VCG", "Bentone Gel CAO V", "Bentone 27 V" and "Bentone Gel MIO V" by Elementis. Montmorillonites and smectites are hydrated aluminum and/or magnesium silicates. Mention may be made, as example, of the montmorillonite sold under the name Gel White H by Rockwood Additives and of the purified smectite sold under the name Veegum Granules by Vanderbilt. Mention may also be made of the montmorillonite sold under the name Kunipia G4 by Kunimine and the sepiolite Pangel S9 sold by Tolsa.

Mention may be made, as examples of kaolinites, of the kaolins sold under the names Coslin C 100 by BASF Personal Care Ingredients or Kaolin Supreme by Imerys.

Talcs are hydrated magnesium silicates usually comprising aluminum silicate. The crystal structure of talc consists of repeated layers of a sandwich of brucite between layers of silica. Mention may be made, as examples, of micronized magnesium silicate with a particle size of 5 microns, sold under the name Micro Ace P3 by Nippon Talc, or the talcs sold under the names Rose Talc and Talc SG-2000 by Nippon Talc, J 68 BC by US Cosmetics (Miyoshi), Luzenac 00 and Luzenac Pharma M by Luzenac and Talc JA-46R by Asada Milling.

Mention may be made, as saponite, which belongs to the family of the montmorillnites, of synthetic saponite, in particular that sold by Kunimine under the Sumecton® name.

Mention may be made, as synthetic laponite, of Laponite XLG, sold by Rockwood.

Preferably, the clay used in the composition of the present invention is chosen from kaolinites and even better kaolin The kaolin is advantageously present under the form of solid particles.

The composition advantageously comprises from 0.5 to 10% by weight of clay(s), preferably kaolinite, even better kaolin, more preferably from 1 to 5% by weight, with regard to the total weight of the composition.

Liquid Fatty Substances

The cosmetic composition, according to the present invention, may further comprise one or more fatty substances that are liquid at room temperature (25° C.) and at atmospheric pressure (1.013*10$^5$ Pa), different from the fatty alcohols and the silicones described above.

The term "fatty substance" means an organic compound that is insoluble in water at ordinary temperature (25° C.) and at atmospheric pressure ($1.013*10^5$ Pa) (solubility of less than 5%, preferably of less than 1% and even more preferentially of less than 0.1%). They have in their structure at least one hydrocarbon-based chain containing at least 6 carbon atoms. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

In addition, the liquid fatty substances of the present invention are nonpolyoxyethylenated and nonpolyglycerolated.

The term "oil" means a "fatty substance" that is liquid at room temperature (25° C.) and at atmospheric pressure ($1.013*10^5$ Pa).

The term "non-silicone oil" means an oil not containing any silicon atoms (Si).

More particularly, the liquid fatty substances can be chosen from $C_6$-$C_{16}$ liquid hydrocarbons, liquid hydrocarbons containing more than 16 carbon atoms, oils of animal origin, triglycerides of plant or synthetic origin, fluoro oils, liquid fatty acid and/or fatty alcohol esters other than triglycerides, and mixtures thereof.

It is recalled that the fatty esters and acids more particularly have at least one linear or branched, saturated or unsaturated hydrocarbon-based group comprising 6 to 30 and better still from 8 to 30 carbon atoms, which is optionally substituted, in particular with one or more hydroxyl groups (in particular 1 to 4). If they are unsaturated, these compounds can comprise one to three conjugated or non-conjugated carbon-carbon double bonds.

As regards the $C_6$-$C_{16}$ liquid hydrocarbons, they are more particularly linear, branched or optionally cyclic, and are preferably alkanes. Examples that may be mentioned include hexane, cyclohexane, undecane, dodecane, tridecane or isoparaffins, such as isohexadecane, isodecane or isododecane, and mixtures thereof.

The linear or branched liquid hydrocarbons of mineral or synthetic origin containing more than 16 carbon atoms are preferably chosen from liquid paraffins, petroleum jelly, liquid petroleum jelly, mineral oil, polydecenes and hydrogenated polyisobutene such as Parleam®, and mixtures thereof.

By way of hydrocarbon-based oils of animal origin, mention may be made of perhydrosqualene.

The triglycerides of vegetable or synthetic origin are preferably chosen from liquid fatty acid triglycerides comprising from 6 to 30 carbon atoms, for instance heptanoic or octanoic acid triglycerides, or alternatively, more particularly from those present in plant oils, for instance coconut oil, sunflower oil, corn oil, soybean oil, marrow oil, grapeseed oil, sesame seed oil, hazelnut oil, apricot oil, macadamia oil, arara oil, castor oil, avocado oil, jojoba oil, shea butter oil or synthetic caprylic/capric acid triglycerides, for instance those sold by the company Stéarineries Dubois or those sold under the names Miglyol® 810, 812 and 818 by the company Dynamit Nobel, and mixtures thereof.

Fluoro oils that may be mentioned include perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

As regards the liquid fatty acid and/or fatty alcohol esters advantageously other than the triglycerides mentioned above and non-silicone waxes, mention may be made especially of esters of saturated or unsaturated, linear $C_1$-$C_{26}$ or branched $C_3$-$C_{26}$ aliphatic monoacids or polyacids and of saturated or unsaturated, linear $C_1$-$C_{26}$ or branched $C_3$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$—$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates; 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate, and mixtures thereof.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds can comprise one to three conjugated or non-conjugated carbon-carbon double bonds.

The esters according to this variant can also be chosen from mono-, di-, tri- and tetraesters, polyesters and mixtures thereof.

These esters may be, for example, oleates, laurates, palmitates, myristates, behenates, cocoates, stearates, linoleates, linolenates, caprates, arachidonates or mixtures thereof, such as, in particular, oleate/palmitate, oleate/stearate or palmitate/stearate mixed esters.

More particularly, use is made of monoesters and diesters and in particular mono- or di-oleate, -stearate, -behenate, -oleopalmitate, -linoleate, -linolenate or -oleostearate of sucrose, of glucose or of methylglucose.

An example that may be mentioned is the product sold under the name Glucate® DO by the company Amerchol, which is a methylglucose dioleate.

Examples of esters or mixtures of esters of sugar and of fatty acid that may also be mentioned include:
the products sold under the names F160, F140, F110, F90, F70 and SL40 by the company Crodesta, respectively denoting sucrose palmitate/stearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose mono laurate;
the products sold under the name Ryoto Sugar Esters, for example referenced B370 and corresponding to sucrose behenate formed from 20% monoester and 80% diester-triester-polyester;
the sucrose mono-dipalmitate/stearate sold by the company Goldschmidt under the name Tegosoft® PSE.

Preferably, the fatty substances, liquid at room temperature (25° C.) and at atmospheric pressure ($1.013*10^5$ Pa), different from the fatty alcohols and the silicones, are chosen from triglycerides of plant origin.

When they are present, the amount of the liquid fatty substances, different from the fatty alcohols and silicones, advantageously ranges from 0.05 to 15% by weight, and more preferentially from 0.1 to 10% by weight, relative to the total weight of the composition.

Additional Surfactants

The composition according to the present invention, may further comprise one or more additional surfactants different from the cationic, amphoteric and zwitterionic surfactants described above, and in particular surfactants chosen from anionic and non ionic surfactants, and preferably from non ionic surfactants.

The nonionic surfactants that may be present in the composition of the present invention are especially described, for example, in the *Handbook of Surfactants* by M. R. Porter, published by Blackie & Son (Glasgow and London), 1991, pp. 116-178. They are especially chosen from fatty alcohols, fatty α-diols, fatty ($C_1$-$C_{20}$)alkylphenols and fatty acids, these compounds being ethoxylated, propoxylated or glycerolated and containing at least one fatty chain comprising, for example, from 8 to 18 carbon atoms, the number of ethylene oxide or propylene oxide groups possibly ranging especially from 1 to 200, and the number of glycerol groups possibly ranging especially from 1 to 30.

Mention may also be made of condensates of ethylene oxide and of propylene oxide with fatty alcohols, ethoxylated fatty amides preferably having from 1 to 30 ethylene oxide units, polyglycerolated fatty amides comprising on average from 1 to 5 glycerol groups, and in particular from 1.5 to 4, ethoxylated fatty acid esters of sorbitan containing from 1 to 30 ethylene oxide units, fatty acid esters of sucrose, fatty acid esters of polyethylene glycol, ($C_6$-$C_{24}$) alkylpolyglycosides, oxyethylenated plant oils, N—($C_6$-$C_{24}$)alkylglucamine derivatives, amine oxides such as ($C_{10}$-$C_{14}$)alkylamine oxides or N—($C_{10}$-$C_{14}$) acylaminopropylmorpholine oxides.

The non ionic surfactants may be present in an amount ranging from 0.1 to 10% by weight, preferably from 0.5 to 5% by weight, with regard to the total weight of the composition.

According to a preferred embodiment, the composition of the invention contains less than 5% by weight of anionic surfactants, preferably less than 1% by weight, and most preferably less than 0.5% by weight, with regard to the total weight of the composition.

Thickening Agents:

The composition according to the invention may further contain additional thickening agents, different from clays, preferably chosen from polymeric thickening agents.

Particularly preferred thickening agent are polymers of natural origin, such as those belonging to the families of celluloses and starches.

Cosmetically Acceptable Medium

The composition according to the present invention, advantageously comprises a cosmetically acceptable medium.

The term "cosmetically acceptable medium" means a medium that is compatible with human keratin fibres, such as the hair.

The cosmetically acceptable medium can be formed from water or from a mixture of water and one or more cosmetically acceptable solvents chosen from $C_1$-$C_4$ lower alcohols, such as ethanol and isopropanol; polyols and polyol ethers, for instance 2-butoxyethanol, propylene glycol, glycerol, propylene glycol monomethyl ether, diethylene glycol monoethyl ether and monomethyl ether, and mixtures thereof.

The cosmetic composition, according to the present invention, advantageously comprises water in an amount preferably ranging from 30 to 98% by weight, more preferentially from 50 to 95% by weigh, and better still from 60 to 90% by weight, relative to the total weight of the composition.

Additives

The cosmetic composition according to the present invention may further comprise one or more additive(s) other than the compounds of the invention.

As additives that may be used in accordance with the invention, mention may be made of solid fatty substances different from fatty alcohols such as waxes, anionic, nonionic or amphoteric polymers or mixtures thereof, antidandruff agents, anti-seborrhoea agents, agents for preventing hair loss and/or for promoting hair regrowth, vitamins and provitamins including panthenol, sunscreens, mineral or organic pigments, sequestrants, plasticizers, solubilizers, acidifying agents, opacifiers or nacreous agents, antioxidants, hydroxy acids, fragrances and preserving agents.

Needless to say, a person skilled in the art will take care to select this or these optional additional compound(s) such that the advantageous properties intrinsically associated with the composition according to the invention are not, or are not substantially, adversely affected by the envisaged addition(s).

The above additives may generally be present in an amount, for each of them, of between 0.001% and 20% by weight, relative to the total weight of the composition.

The present invention also relates to a process for washing keratin fibres, which consists in applying to the said keratin fibres an effective amount of a composition as described above, and after an optional leave-on time, removing it by rinsing.

The leave-on time of the composition on the keratin fibres may range from a few seconds to 15 minutes, better still from 5 seconds to 10 minutes and even better still from 10 seconds to 5 minutes.

The composition may be applied to wet or dry keratin fibres.

Finally, the present invention relates to the use of a composition as described above for washing keratin fibres.

In the present invention, the term "keratin fibres" denotes human keratin fibres, and in particular human hair.

The examples that follow serve to illustrate the invention without, however, being limiting in nature.

EXAMPLE

In the examples that follow and unless otherwise indicated, all amounts are given as mass percentages of active material relative to the total weight of the composition (% AM=% active matter).

The following composition was prepared from the ingredients indicated in the table below.

| Ingredients | Amounts (% wt AM) |
| --- | --- |
| HYDROXYPROPYL STARCH PHOSPHATE | 1.75 |
| HYDROXYETHYLCELLULOSE | 0.3 |
| BRASSICA CAMPESTRIS (RAPESEED) SEED OIL | 1 |
| CETYL ALCOHOL | 2.5 |
| BEHENTRIMONIUM CHLORIDE | 0.395 |
| COCAMIDOPROPYL BETAINE | 1.15 |
| COCAMIDE MEA | 1 |
| GLYCERIN | 0.5 |
| DIMETHICONE (and) AMODIMETHICONE (and) TRIDECETH-10 (and) PEG-100 STEARATE (and) STEARETH-6 (and) TRIDECETH-3 | 5% (2% AM dimethicone 0.5% AM amodimethicone) |
| GUAR HYDROXYPROPYLTRIMONIUM CHLORIDE | 0.15 |
| PEG-45M | 0.01 |
| KAOLIN | 2 |
| WATER | Qsp 100 |

The above composition was used a shampoo and applied onto wet hair.

This composition exhibited very good cleaning properties. The foam formed by massaging the composition spread easily and uniformly onto the wet hair.

The hair washed with this composition was perfectly clean, and exhibited good conditioning properties. The hair was smooth, soft and easy to disentangle without substantial breaking thereof.

The invention claimed is:

1. Cosmetic composition comprising:
one or more cationic surfactants,
one or more amphoteric or zwitterionic surfactants,
one or more silicones,
one or more cationic polymers,
one or more fatty alcohols, and
one or more clays, in an amount ranging from 1% to 5% by weight, with regard to the total weight of the composition;
wherein the composition does not comprise an anionic surfactant; and
wherein the composition further comprises at least one nonionic surfactant.

2. Composition according to claim 1, wherein the clays are chosen from kaolinites, montmorillonites, saponites, laponites, bentonites, hectorites and illites.

3. Composition according to claim 1, wherein the cationic surfactants are chosen from:
primary, secondary or tertiary fatty amines, optionally polyoxyalkylenated,
quaternary ammonium salts of general formula (IV)

wherein,
$R_8$ to $R_{11}$, which may be identical or different, represent a linear or branched aliphatic group comprising from 1 to 30 carbon atoms, or an aromatic group it being understood that at least one of the groups $R_8$ to $R_{11}$ comprises from 12 to 22 carbon atoms; and
$X^-$ represents an organic or mineral anionic counterion chosen from halides, acetates, phosphates, nitrates, $(C_1-C_4)$alkyl sulfates, $(C_1-C_4)$alkyl- or $(C_1-C_4)$alkylaryl sulfonates;
quaternary ammonium salts of imidazoline of formula (V)

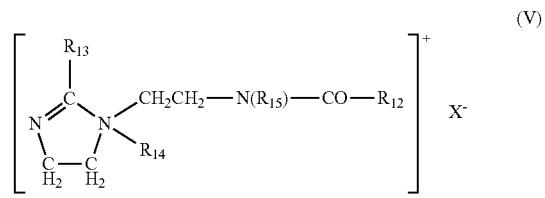

wherein, $R_{12}$ represents an alkyl or alkenyl group comprising from 8 to 30 carbon atoms, $R_{13}$ represents a hydrogen atom, a $C_1-C_4$ alkyl group or an alkyl or alkenyl group comprising from 8 to 30 carbon atoms, $R_{14}$ represents a $C_1-C_4$ alkyl group, $R_{15}$ represents a hydrogen atom or a $C_1-C_4$ alkyl group; $X^-$ is an anion chosen from the group of halides, phosphates, acetates, lactates, alkyl sulfates, alkyl- or alkylarylsulfonates in which the alkyl and aryl groups each comprise from 1 to 20 carbon atoms and from 6 to 30 carbon atoms;
di- or tri-quaternary ammonium salts of formula (VI)

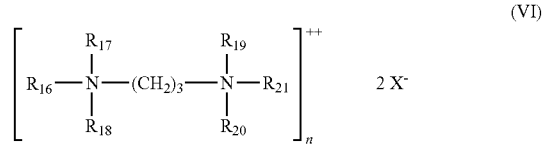

wherein, $R_{16}$ denotes an alkyl radical comprising from 16 to 30 carbon atoms which is optionally hydroxylated and/or interrupted by one or more oxygen atoms, $R_{17}$ is chosen from hydrogen and an alkyl radical comprising from 1 to 4 carbon atoms and an $(R_{16a})(R_{17a})(R_{18a})$N—$(CH_2)_3$ group, $R_{16a}$, $R_{17a}$, $R_{18a}$, $R_{18}$, $R_{19}$, $R_{20}$ and $R_{21}$, which may be identical or different, are chosen from hydrogen and an alkyl radical comprising from 1 to 4 carbon atoms and X⁻ is an anion chosen from the group of halides, acetates, phosphates, nitrates and methyl sulfates; and quaternary ammonium salts containing at least one ester function of formula (VII)

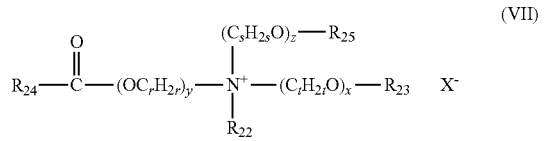

(VII)

wherein,
$R_{22}$ is chosen from $C_1$-$C_6$ alkyl groups and $C_1$-$C_6$ hydroxyalkyl or dihydroxyalkyl groups;
$R_{23}$ is chosen from:
  the group

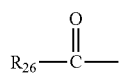

groups $R_{27}$, which are linear or branched, saturated or unsaturated $C_1$-$C_{22}$ hydrocarbon-based groups,
  a hydrogen atom,
$R_{25}$ is chosen from:
  the group

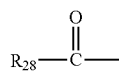

groups $R_{29}$, which are linear or branched, saturated or unsaturated $C_1$-$C_6$ hydrocarbon-based groups,
  a hydrogen atom,
$R_{24}$, $R_{26}$ and $R_{28}$, which may be identical or different, are chosen from linear or branched, saturated or unsaturated $C_7$-$C_{21}$ hydrocarbon-based groups;
r, s and t, which may be identical or different, are integers ranging from 2 to 6;
y is an integer ranging from 1 to 10;
x and z, which may be identical or different, are integers ranging from 0 to 10;
X⁻ is a simple or complex, organic or mineral anion;
with the proviso that the sum x+y+z is from 1 to 15, that when x is 0 then $R_{23}$ denotes $R_{27}$, and that when z is 0 then $R_{25}$ denotes $R_{29}$.

4. Composition according to claim 1, wherein the amount of cationic surfactants ranges from 0.05 to 10% by weight, relative to the total weight of the composition.

5. Composition according to claim 1, wherein the amphoteric or zwitterionic surfactants are chosen from ($C_8$-$C_{20}$) alkylbetaines, sulfobetaines, ($C_8$-$C_{20}$alkyl)amido($C_3$-$C_8$alkyl)betaines or ($C_8$-$C_{20}$alkyl)amido($C_6$-$C_8$alkyl) sulfobetaines.

6. Composition according to claim 1, wherein the amount of the amphoteric or zwitterionic surfactant(s) ranges from 0.05% to 15% by weight, relative to the total weight of the composition.

7. Composition according to claim 1, wherein it contains one or more non-amino silicone and one or more amino silicone.

8. Composition according to claim 7, wherein the non-amino silicone and the amino silicone are both present in the composition in the form of emulsions.

9. Composition according to claim 1, wherein the total amount of silicone(s) ranges from 0.5 to 15% by weight, relative to the total weight of the composition.

10. Composition according to claim 1, wherein the cationic polymers are chosen from:
  (1) homopolymers or copolymers derived from acrylic or methacrylic esters or amides and comprising at least one of the units of formulae (VIII), (IX), (X) and (XI) below:

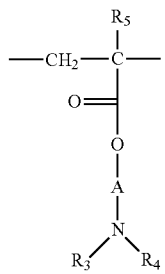

(VIII)

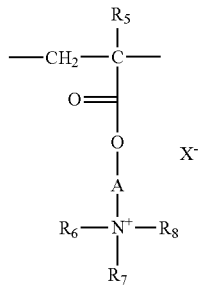

(IX)

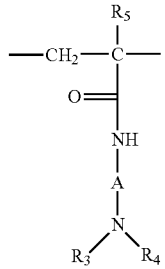

(X)

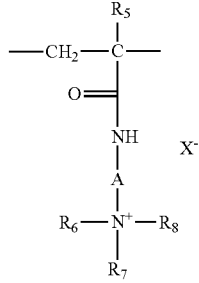

(XI)

wherein,
  $R_3$ and $R_4$, which may be identical or different, represent a hydrogen atom or an alkyl group containing from 1 to 6 carbon atoms, $R_5$, which may be identical or different, denote a hydrogen atom or a $CH_3$ group, A, which may be identical or different, represent a linear or branched alkyl group of 1 to 6 carbon atoms, or a hydroxyalkyl group comprising 1 to 4 carbon atoms, $R_6$, $R_7$ and $R_8$, which may be identical or different, represent an alkyl group containing from 1 to 18 carbon atoms or a benzyl group, and $X^-$ denotes an anion derived from a mineral or organic acid, (2) polymers formed from piperazinyl units and divalent alkylene or hydroxyalkylene radicals containing straight or branched chains, optionally interrupted with oxygen, sulfur or nitrogen atoms or with aromatic or heterocyclic rings, and also the oxidation and/or quaternization products of these polymers;

(3) water-soluble polyamino amides prepared by polycondensation of an acidic compound with a polyamine, these polyaminoamides being optionally crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative, the crosslinking agent being used in proportions ranging from 0.025 to 0.35 mol per amine group of the polyaminoamide;

(4) Polyaminoamide derivatives resulting from the condensation of polyalkylene polyamines with polycarboxylic acids followed by alkylation with difunctional agents;

(5) The polymers obtained by reaction of a polyalkylene polyamine comprising two primary amine groups and at least one secondary amine group with a dicarboxylic acid chosen from diglycolic acid and saturated aliphatic dicarboxylic acids having from 3 to 8 carbon atoms;

(6) Cyclopolymers of alkyldiallylamine or of dialkyldiallylammonium comprising, as main constituent of the chain, units corresponding to formula (XII) or (XIII):

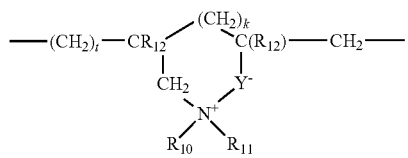

(XII)

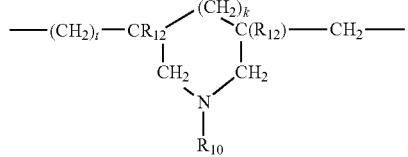

(XIII)

wherein, k and t are equal to 0 or 1, the sum k+t being equal to 1; $R_{12}$ denotes a hydrogen atom or a methyl group; $R_{10}$ and $R_{11}$, independently of each other, denote an alkyl group containing from 1 to 6 carbon atoms, a hydroxyalkyl group in which the alkyl group contains 1 to 5 carbon atoms, a lower ($C_1$-$C_4$) amidoalkyl group, or $R_{10}$ and $R_{11}$ may denote, together with the nitrogen atom to which they are attached, heterocyclic groups such as piperidyl or morpholinyl; $Y^-$ is an anion such as bromide, chloride, acetate, borate, citrate, tartrate, bisulfate, bisulfite, sulfate or phosphate;

(7) The quaternary diammonium polymer containing repeating units corresponding to the formula (XIV):

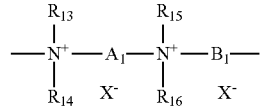

(XIV)

wherein, $R_{13}$, $R_{14}$, $R_{15}$ and $R_{16}$, which may be identical or different, represent aliphatic, alicyclic or arylaliphatic groups containing from 1 to 20 carbon atoms or lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ represent a linear or branched $C_1$-$C_6$ alkyl group substituted with a nitrile, ester, acyl or amide group or a group $COOR_{17}D$ or $CONHR_{17}D$ where $R_{17}$ is an alkylene and D is a quaternary ammonium group, $A_1$ and $B_1$ represent polymethylene groups containing from 2 to 20 carbon atoms which may be linear or branched, and saturated or unsaturated, and which may contain, linked to or inserted in the main chain, one or more aromatic rings, or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid;

$A_1$, $R_{13}$ and $R_{15}$ can form, with the two nitrogen atoms to which they are attached, a piperazine ring;

if $A_1$ denotes a linear or branched, saturated or unsaturated alkylene or hydroxyalkylene radical, $B_1$ may also denote a group $(CH_2)_n$—CO-D-OC—$(CH_2)_p$—, n and p are integers ranging from 2 to 20, in which D denotes:

a) a glycol residue of formula: —O—Z—O—, where Z denotes a linear or branched hydrocarbon-based radical or a group corresponding to one of the following formulae:

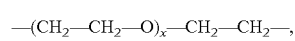

in which x and y denote an integer from 1 to 4, representing a defined and unique degree of polymerization or any number from 1 to 4 representing an average degree of polymerization, b) a bis-secondary diamine residue, c) a bis-primary diamine residue of formula: —NH—Y—NH—, where Y denotes a linear or branched hydrocarbon-based radical, or else the divalent radical —$CH_2$—$CH_2$—S—S—$CH_2$—$CH_2$—, d) a ureylene group of formula —NH—CO—NH—, (8) Polyquaternary ammonium polymers formed especially from units of formula (XVI):

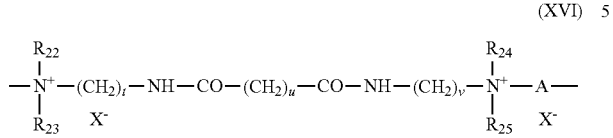 (XVI)

wherein,

R$_{22}$, R$_{23}$, R$_{24}$ and R$_{25}$, which may be identical or different, represent a hydrogen atom or a methyl, ethyl, propyl, β-hydroxyethyl, β-hydroxypropyl or —CH$_2$CH$_2$(OCH$_2$CH$_2$)$_p$OH group, where p is equal to 0 or to an integer between 1 and 6, with the proviso that R$_{22}$, R$_{23}$, R$_{24}$ and R$_{25}$ do not simultaneously represent a hydrogen atom, t and u, which may be identical or different, are integers between 1 and 6, v is equal to 0 or to an integer between 1 and 34, X$^-$ denotes an anion, and A denotes a dihalide radical;

(9) Quaternary polymers of vinylpyrrolidone and/or of vinylimidazole;

(10) Cationic polysaccharides;

(11) Cationic proteins or cationic protein hydrolysates, polyalkyleneimines, polymers containing vinylpyridine or vinylpyridinium units, condensates of polyamines and of epichlorohydrin, quaternary polyureylenes and chitin derivatives;

(12) Polyamines; and

(13) Polymers comprising in their structure:

(a) one or more units corresponding to formula (A) below:

(b) optionally one or more units corresponding to formula (B) below:

11. Composition according to claim 10, wherein it contains one or more cationic polymer belonging to family (10).

12. Composition according to claim 1, wherein the amount of cationic polymer(s) ranges from 0.01 to 10% by weight, with regard to the total weight of the composition.

13. Composition according to claim 1, wherein the fatty alcohols are chosen from the compounds of formula (I)

wherein R denotes a saturated or unsaturated, linear or branched radical containing from 8 to 30.

14. Composition according to claim 1, wherein the fatty alcohols are solid at room temperature (25° C.) and at atmospheric pressure (1.013*10$^5$ Pa).

15. Composition according to claim 14, wherein the fatty alcohols are chosen from cetyl alcohol, stearyl alcohol, and mixtures thereof.

16. Composition according to claim 1, wherein the amount of fatty alcohols ranges from 0.05 to 15% by weight, relative to the total weight of the composition.

17. Process for washing keratin fibres, wherein a composition according to claim 1 is applied on said keratin fibres.

* * * * *

UNITED STATES PATENT AND TRADEMARK OFFICE
CERTIFICATE OF CORRECTION

| | |
|---|---|
| PATENT NO. | : 11,246,824 B2 |
| APPLICATION NO. | : 16/314836 |
| DATED | : February 15, 2022 |
| INVENTOR(S) | : D. Roy et al. |

It is certified that error appears in the above-identified patent and that said Letters Patent is hereby corrected as shown below:

In the Specification

| Column | Line | |
|---|---|---|
| 35 | 11 | change "acid," to -- acid; --. |
| 36 | 4 | change "bisulfate" to -- bisulfite --. |

Signed and Sealed this
Twenty-first Day of February, 2023

Katherine Kelly Vidal
Director of the United States Patent and Trademark Office